(12) United States Patent
Kasuya et al.

(10) Patent No.: US 9,186,069 B2
(45) Date of Patent: Nov. 17, 2015

(54) BIOLOGICAL INFORMATION DISPLAYING APPARATUS AND BIOLOGICAL INFORMATION DISPLAYING SYSTEM

(71) Applicant: NIHON KOHDEN CORPORATION, Tokyo (JP)

(72) Inventors: Hiromitsu Kasuya, Tokyo (JP); Rie Tanaka, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 105 days.

(21) Appl. No.: 14/045,485

(22) Filed: Oct. 3, 2013

(65) Prior Publication Data

US 2014/0125477 A1 May 8, 2014

(30) Foreign Application Priority Data

Nov. 8, 2012 (JP) ................................. 2012-246399

(51) Int. Cl.
| | |
|---|---|
| G08B 25/00 | (2006.01) |
| A61B 5/02 | (2006.01) |
| A61B 5/0205 | (2006.01) |
| A61B 5/00 | (2006.01) |
| G06F 19/00 | (2011.01) |
| A61B 5/044 | (2006.01) |
| A61B 5/0215 | (2006.01) |

(52) U.S. Cl.
CPC ................. *A61B 5/02* (2013.01); *A61B 5/0002* (2013.01); *A61B 5/0205* (2013.01); *A61B 5/02055* (2013.01); *A61B 5/044* (2013.01); *A61B 5/7445* (2013.01); *G06F 19/345* (2013.01); *G06F 19/3406* (2013.01); *G06F 19/3418* (2013.01); *A61B 5/0022* (2013.01); *A61B 5/02152* (2013.01)

(58) Field of Classification Search
CPC ............................ A61B 5/0002; A61B 5/0205; G06F 19/3406; G06F 19/3418; G06Q 50/22
USPC ........... 340/525, 539.12, 573.1; 600/300, 301
See application file for complete search history.

(56) References Cited

U.S. PATENT DOCUMENTS

| | | |
|---|---|---|
| 2007/0156031 A1 | 7/2007 | Sullivan et al. |
| 2008/0183054 A1 | 7/2008 | Kroeger et al. |
| 2010/0222650 A1* | 9/2010 | Tanishima et al. ............ 600/301 |

FOREIGN PATENT DOCUMENTS

| | | |
|---|---|---|
| JP | 56-46728 Y2 | 11/1981 |
| JP | 11-290282 A | 10/1999 |

OTHER PUBLICATIONS

The extended European Search Report for the related European Patent Application No. 13189250.7 dated Mar. 19, 2014.

*Primary Examiner* — John A Tweel, Jr.
(74) *Attorney, Agent, or Firm* — Kenealy Vaidya LLP (57) ABSTRACT

A biological information displaying apparatus includes: a displaying section on which a measurement display screen displaying biological information under measurement and an abnormality display screen displaying information alarming an abnormality of the biological information, and the biological information at a timing when the abnormality occurs are displayed; and a display controlling section which is configured to display the abnormality display screen on the measurement display screen, so that the abnormality display screen is superimposed on the measurement display screen. In case where the abnormality display screen is displayed on the displaying section, the display controlling section controls the displaying section so that, even when the abnormality resolves, the information alarming the abnormality of the biological information, and the biological information at the timing when the abnormality occurs are continued to be displayed on the abnormality display screen.

7 Claims, 8 Drawing Sheets

BIOLOGICAL INFORMATION DISPLAYING APPARATUS AND BIOLOGICAL INFORMATION DISPLAYING SYSTEM

CROSS-REFERENCE TO RELATED APPLICATION(S)

This application is based upon and claims the benefit of priority from prior Japanese patent application No. 2012-246399 filed on Nov. 8, 2012, the entire contents of which are incorporated herein by reference.

BACKGROUND

The presently disclosed subject matter relates to a biological information displaying apparatus and biological information displaying system for displaying biological information detected from the subject, on a display screen.

A related-art apparatus has been proposed which collects biological information of the subject, and which displays the collected biological information. For example, JP-UM-B-56-046728 discloses a memory monitor which, at an alarm time, displays the waveform of a biological signal of a patient in a form of a broken line, so as to clearly indicate an alarm condition to a monitoring person. In the memory monitor, the waveforms of biological signals of a plurality of patients are displayed on a cathode ray tube, and, when biological information in an alarm condition is produced, only the biological signal waveform of the patient in which the alarm condition occurs is displayed in a form of a broken line. This enables the alarm condition to be clearly indicated to the monitoring person, and an alarm lamp or buzzer to be omitted from an operation panel, and is effectively used in patient monitoring.

JP-A-11-290282 discloses a patient monitoring system which, in accordance with the clinical state and symptom of the patient, can express the setting of alarm values and notification according to the contents of instructions from the doctor. In the patient monitoring system, when departing from the range of determination conditions, alarm notification is performed, and procedures such as "Doctor call", "Medication", and the like are displayed on a displaying section so that adequate procedures can be performed in response to the alarm notification. Also the observation waveform which is the monitoring information at the timing of the alarm generation is displayed on a display screen, thereby preventing the alarm from being erroneously recognized, and enabling the procedure to be performed rapidly and adequately when the alarm is generated.

In the configuration of the memory monitor disclosed in JP-UM-B-56-046728, at an alarm time, the biological signal waveform of the patient is displayed in a form of a broken line, but, when the biological signal waveform is recovered from the abnormal or alarm condition, the display mode is returned from the display in a form of a broken line to the normal display mode. In the case where, at the alarm time, the monitoring person misses the displaying section of the memory monitor, therefore, the monitoring person hardly recognizes that an alarm was issued in the past, and hence there is a possibility that an adequate procedure cannot be performed when an abnormal condition is generated. Also, there is another problem in that it is difficult to instantly determine whether a past alarm is caused by contamination by an artifact or not.

In the configuration of the patient monitoring system disclosed in JP-A-11-290282, the displaying section on which the contents of the procedure with respect to the alarm notification and monitoring information are displayed is a displaying section (a displaying section at a position which is separated from apparatuses for monitoring patients) of a data processing unit to which measurement data are transmitted from apparatuses for monitoring patients. On the displaying section, monitoring information at the alarm notification is displayed, but monitoring information under measurement, or monitoring information related to monitoring information of alarm notification is not displayed. Therefore, monitoring information which is a cause of alarm notification cannot be checked on the side of the patient, and sets of monitoring information cannot be subjected to comparative determination. Consequently, procedures ("Doctor call", "Medication", and the like) which are previously instructed and stored in accordance with instructions of the doctor can be performed, but it is difficult to rapidly perform other adequate procedures.

SUMMARY

The presently disclosed subject matter may provide a biological information displaying apparatus and biological information displaying system which can surely prevent an alarm that was issued in the past, from being missed, and which can promptly determine whether a past alarm is an erroneous alarm due to, for example, contamination by an artifact or not.

The biological information displaying apparatus may comprise: a displaying section on which a measurement display screen and an abnormality display screen are displayed, the measurement display screen displaying biological information under measurement, the abnormality display screen displaying information alarming an abnormality of the biological information, and the biological information at a timing when the abnormality occurs; and a display controlling section which is configured to control the displaying section, the display controlling section which is configured to display the abnormality display screen on the measurement display screen, based on a preset alarm condition, so that at least a part of the abnormality display screen is superimposed on the measurement display screen, wherein, in a case where the abnormality display screen is displayed on the displaying section, the display controlling section controls the displaying section so that, even when the abnormality resolves, the information alarming the abnormality of the biological information, and the biological information at the timing when the abnormality occurs are continued to be displayed on the abnormality display screen.

In the case where the abnormality display screen is displayed on the displaying section, the display controlling section may control the displaying section so that the information alarming the abnormality of the biological information, and the biological information at the timing when the abnormality occurs are continued to be displayed on the abnormality display screen, until a confirmation process is executed in response to an external operation.

The biological information may include first biological information and second biological information which are different from each other. The abnormality may occur in the first biological information. The first biological information may be related to the second biological information. The display controlling section controls the displaying section so that the second biological information is displayed on the abnormality display screen in addition to the first biological information.

The first biological information and the second biological information may be displayed on the abnormality display screen by a waveform and a numerical value.

The first biological information which is displayed on the abnormality display screen may be an electrocardiogram waveform, and the second biological information may include at least an invasive blood pressure waveform.

The abnormality display screen may be superimposed on a part of the measurement display screen.

The biological information displaying system may incorporate a plurality of the biological information displaying apparatuses connected to a network. Biological information displayed in each of the biological information displaying apparatuses is displayable in another biological information displaying apparatus connected to the network.

DETAILED DESCRIPTION OF EXEMPLARY EMBODIMENTS

Hereinafter, embodiments of the biological information displaying apparatus and biological information displaying system of the presently disclosed subject matter will be described with reference to the accompanying drawings.

Figure 1:
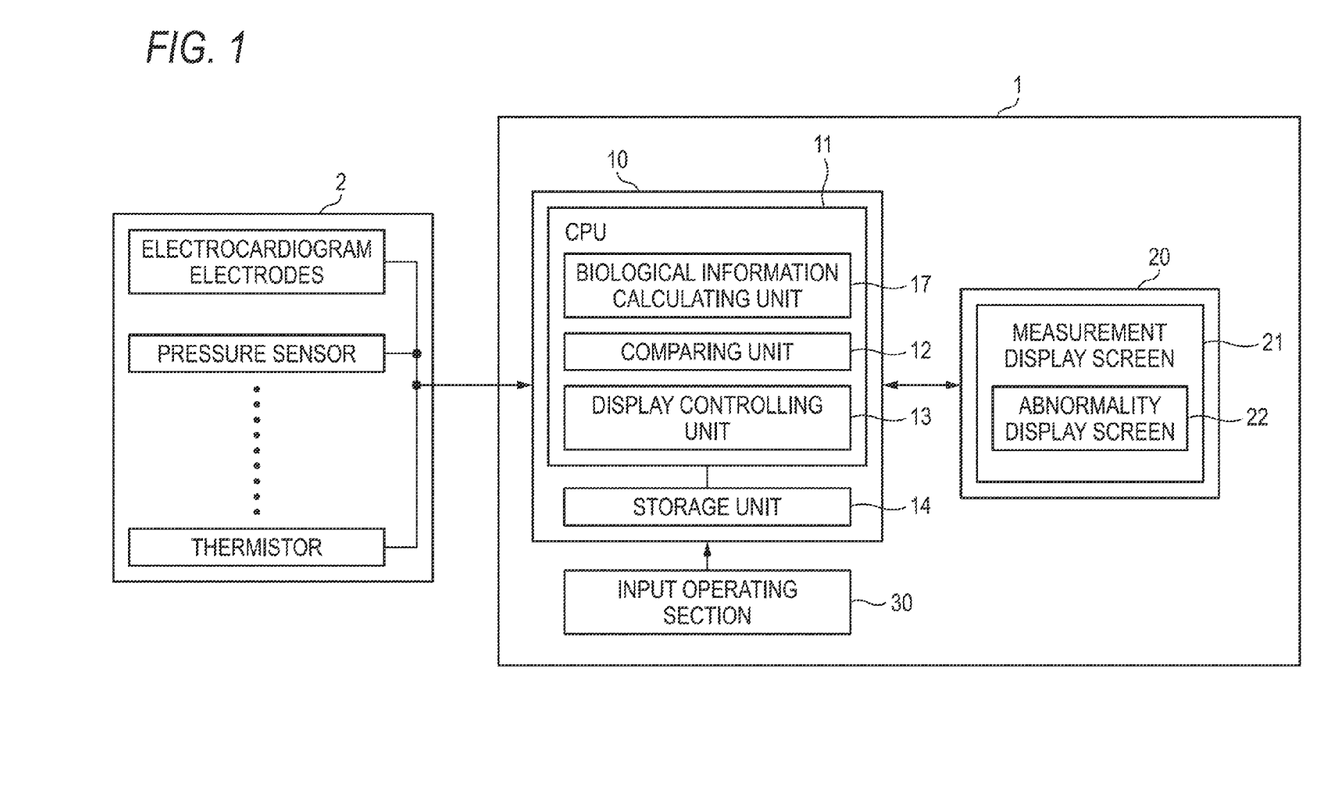
FIG. 1 is a block diagram showing the configuration of a biological information displaying apparatus of the presently disclosed subject matter.

FIG. 1 shows an embodiment of the biological information displaying apparatus. The biological information displaying apparatus 1 is a displaying apparatus which is used for each subject, and which is a so-called bedside monitor. Biological information acquiring units 2 configured by sensors, probes, and the like for measuring biological information such as the electrocardiac signal, the blood pressure value, the blood oxygen saturation, the inspiration oxygen concentration, the body temperature, the expiration carbon dioxide concentration, and the respiratory condition are connected to the biological information displaying apparatus 1. Specific examples of the biological information acquiring units 2 are electrocardiogram electrodes for detecting the electrocardiac signal, a pressure sensor for detecting the non-invasive blood pressure value, an $SpO_2$ probe for detecting the blood oxygen saturation and the pulse wave, an oxygen sensor for detecting the inspiration oxygen concentration, a thermistor for detecting the body temperature, a carbon dioxide sensor for detecting the expiration carbon dioxide concentration, a thermistor for detecting respiration, and like sensors. The biological information acquiring units 2 are attached to the subject, and biological information acquired by the biological information acquiring units 2 are supplied to the biological information displaying apparatus 1.

The biological information displaying apparatus includes a controlling section 10 which controls the operation of the apparatus, a displaying section 20 on which measured biological information is displayed, and an input operating section 30 through which set values related to biological information are input. Biological signals acquired by the biological information acquiring units 2 are supplied to the controlling section 10 of the biological information displaying apparatus 1.

The controlling section 10 controls operations of the sections of the biological information displaying apparatus 1 based on information supplied from the biological information acquiring units 2 and the input operating section 30, and is mainly configured by a CPU (Central Processing Unit) 11. A storage unit 14 such as a hard disk drive and electronic memories are connected to the CPU 11. The CPU 11 executes various numerical calculations, information processing, and operation controls in accordance with programs stored in the storage unit 14, and has functions of a comparing unit 12, a display controlling unit 13, and a biological information calculating unit 17.

The biological information calculating unit 17 applies predetermined arithmetic processing to the biological signals supplied from the biological information acquiring units 2, and outputs each processed signal as biological information.

The comparing unit 12 performs a comparison process between the sets of biological information which are arithmetically processed in the biological information calculating unit 17, and preset thresholds for the respective sets of biological information. Here, the thresholds for the biological information includes not only values indicating the maximum value (allowable range) of dispersion of biological information which can be allowed for the subject, but also values which are not limited to the allowable range, and which are uniquely set. For example, the values which are uniquely set are values that can be set by a medical person in a case such as that where the number, time period, and the like of occasions where biological information of the subject exceeds a predetermined value are to be checked. The comparison process performs not only comparisons between values (for example, the heart rate and the blood pressure value) of the biological information, but also those between the shapes of waveforms for abnormality determination, and the like. In the comparison of the shapes of waveforms, for example, an electrocardiogram waveform is compared with a basic waveform, and, based on the approximation, it is determined whether arrhythmia occurs or not. The comparing unit 12 always performs a comparing process of determining whether biological information under measurement exceeds (or falls below) the threshold or not, or comparing to determine whether the waveform approximates the basic waveform or not, or when arrhythmia occurs or not, and determines timings of generation and detection of an abnormal value, and an announcement timing of an alarm. In the above-described comparing process, also detachment of the electrodes (an abnormality that the waveform cannot be detected) is determined in addition to an abnormality of biological information.

The display controlling unit 13 performs controlling processes of causing biological information (biological information under measurement) which is measured by the biological information acquiring units 2, and which is calculated in the biological information calculating unit 17, to be displayed on the displaying section 20, and, when biological information is acquired by the biological information acquiring units 2, causing an occurrence of an abnormality to be displayed on the displaying section 20. When biological information under measurement is transmitted from the biological information calculating unit 17, the display controlling unit 13 transmits a control signal instructing that the biological information under measurement be displayed, to the displaying section 20. In the case where, as a result of the comparing process by the comparing unit 12, it is determined that the measured biological information is abnormal (if alarm conditions are satisfied), the display controlling unit 13 transmits a control signal instructing that an occurrence of an abnormality in biological information be displayed, to the displaying section 20. The display controlling unit 13 is an example of the display controlling section.

For example, an occurrence of an abnormality in biological information can be notified by visually or aurally displaying information indicating that the abnormality is alarmed, or displaying biological information at the timing when the abnormality occurs. As a display indicating an occurrence of an abnormality, specifically, a display in a mode which can be visually recognized in an easy manner, such as that an alarm message such as "Biological information alarm" is displayed, or that an alarm symbol is displayed may be employed. As a display of biological information at the timing when the abnormality occurs, a display in which a measurement waveform (abnormal waveform) or measurement value (abnormal value) at the timing of the occurrence of the abnormality of the biological information which is determined abnormal may be displayed, or alternatively the measurement waveform or value of biological information related to the biological information at the timing when the abnormality occurs may be displayed in addition to the abnormal waveform (abnormal value). For example, the measurement waveform means the electrocardiogram waveform, the blood pressure waveform, the pulse wave, the respiratory waveform, and the like, and measurement value means the heart rate, the blood pressure value, the blood oxygen saturation, the body temperature, the respiratory rate, the carbon dioxide concentration, the expiration carbon dioxide concentration, the inspiration oxygen concentration, and the like.

The storage unit 14 stores the above-described programs, and further stores and holds: the sets of biological information which are acquired by the biological information acquiring units 2, and which are arithmetically processed in the biological information calculating unit 17; the preset thresholds for the sets of biological information; biological information at the timing when an abnormality occurs; messages which are to be displayed on the display screen of the displaying section 20 when an abnormality occurs; etc. Examples of the stored and held biological information are waveform biological information such as the electrocardiogram waveform, the pulse waveform, the invasive blood pressure waveform, and the respiratory waveform, and numerical biological information such as the heart rate, the pulse rate, the blood pressure value, the oxygen saturation, the carbon dioxide concentration, the respiratory rate, and the body temperature.

The displaying section 20 displays biological information on the display screen based on the control signal supplied from the display controlling unit 13. On the displaying section 20, displayed are a measurement display screen 21 on which biological information measured by the biological information acquiring units 2 is displayed in real time, and an abnormality display screen 22 on which, when an abnormality occurs in the biological information under measurement (when the alarm conditions are satisfied), the occurrence of the abnormality is displayed. The abnormality display screen 22 is a screen which is displayed on the measurement display screen 21 when an abnormality occurs in biological information, and hence may be displayed, for example, in a pop up manner when an abnormality occurs in the biological information.

In the abnormality display screen 22, preferably, biological information (an abnormal waveform, an abnormal value, and the like) which is displayed on the screen, and the biological waveform or numerical value under measurement which is displayed on the measurement display screen 21 are displayed in a manner that they are easily compared with each other. Therefore, it is preferred that the abnormality display screen 22 is superimposedly displayed on a part of the display screen area of the measurement display screen 21. Moreover, it is preferred that the abnormality display screen 22 is displayed at a position where the biological waveform or numerical value which is in the biological waveforms or numerical values displayed on the measurement display screen 21, and which is used as a target for comparison is not masked. In order to more easily compare with the biological waveform or numerical value under measurement, the abnormality display screen 22 may be enabled to be dragged. The abnormality display screen 22, and biological information and the like (such as the information indicating that an abnormality occurs, the detected abnormal waveform at the timing when the abnormality occurs, a waveform related to the abnormal waveform, and the like) displayed thereon are not erased even the abnormality resolves, and are continued to be displayed until a confirmation process is executed in response to an external operation.

The input operating section 30 is configured by a keyboard, a mouse, a touch panel, a portable communication terminal, or the like. The input operating section 30 is connected to the controlling section 10, and, when an inputting operation is performed, the thresholds for the sets of biological information, contents of messages which are to be displayed on the abnormality display screen 22 when an abnormality occurs, the kind of the measurement waveform or measurement value which is to be displayed on the abnormality display screen 22 when an abnormality occurs, and the like can be set.

In the above-described configuration, when the comparing unit 12 determines that an abnormality occurs in the measured biological information, the display controlling unit 13 controls the displaying section 20 so that the abnormality display screen 22 is displayed, and the displayed abnormality display screen 22 is not erased even when the abnormality resolves, and is continuously displayed until an abnormality display screen confirmation process is executed in response to an external operation by a medical person. Therefore, also the information indicating that the abnormality is alarmed, and the biological information at the timing when the abnormality occurs are continued to be displayed on the abnormality display screen 22 until the confirmation process is executed.

In order to surely prevent an occurrence of an abnormality from being missed or overlooked, preferably, the process of erasing the abnormality display screen 22 may be configured by a plurality of steps of process. For example, a work of pressing an alarm confirmation button indicating that the alarm is confirmed is first performed. Then, a work of pressing a content confirmation button indicating that the contents of a message displayed on the screen, and contents which are displayed on the screen, such as the measurement waveform at the timing when the abnormality occurs are confirmed is performed. A work of pressing an erasure confirmation button indicating that, as a result of the confirmation work, it is determined that the abnormality display screen 22 may be erased is further performed. When the three steps of process are sequentially implemented, the display controlling unit 13 may deem that the analysis of the contents of the alarm is ended, and erase the abnormality display screen 22.

The abnormality display screen 22 may display only particular abnormalities. Examples of the particular abnormalities are an abnormality having a high priority (seriousness or the like), an abnormality related to a specific symptom or organ (an abnormality related to the heart or the like), and an abnormality related to a specific parameter (an electrocardiogram or the like). All abnormalities including a technical alarm are always displayed on the upper portion of the measurement display screen 21 (although not shown, for example, the left side of the alarm symbol 42 in FIG. 2). The display is configured only by a message alarm indicating the contents of the abnormality, and, when the cause is eliminated, automatically erased.

Next, specific examples of biological information to be displayed on the screens of the displaying section 20 will be described.

Figure 2:
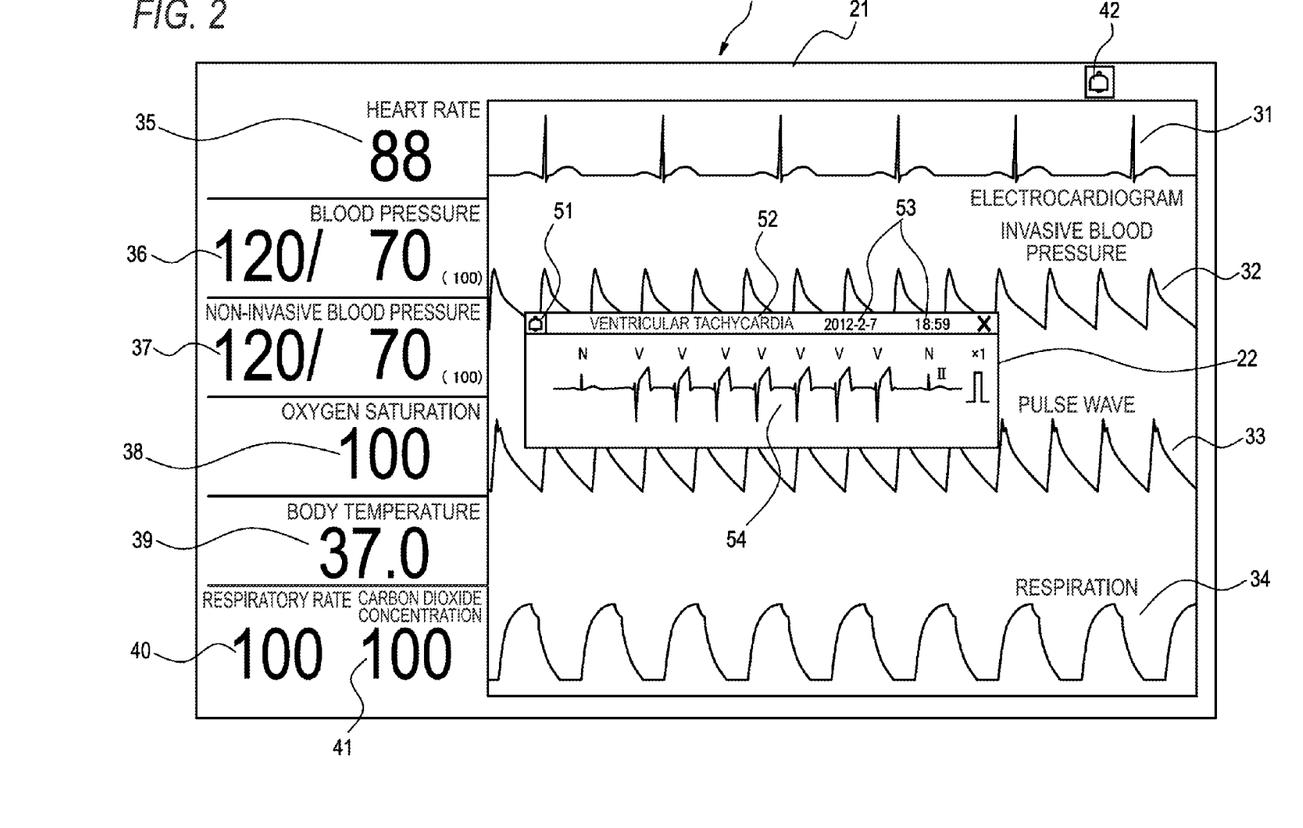
FIG. 2 is a view showing a specific example of biological information of an abnormality display screen which is displayed on a measurement display screen.
Figure 3:
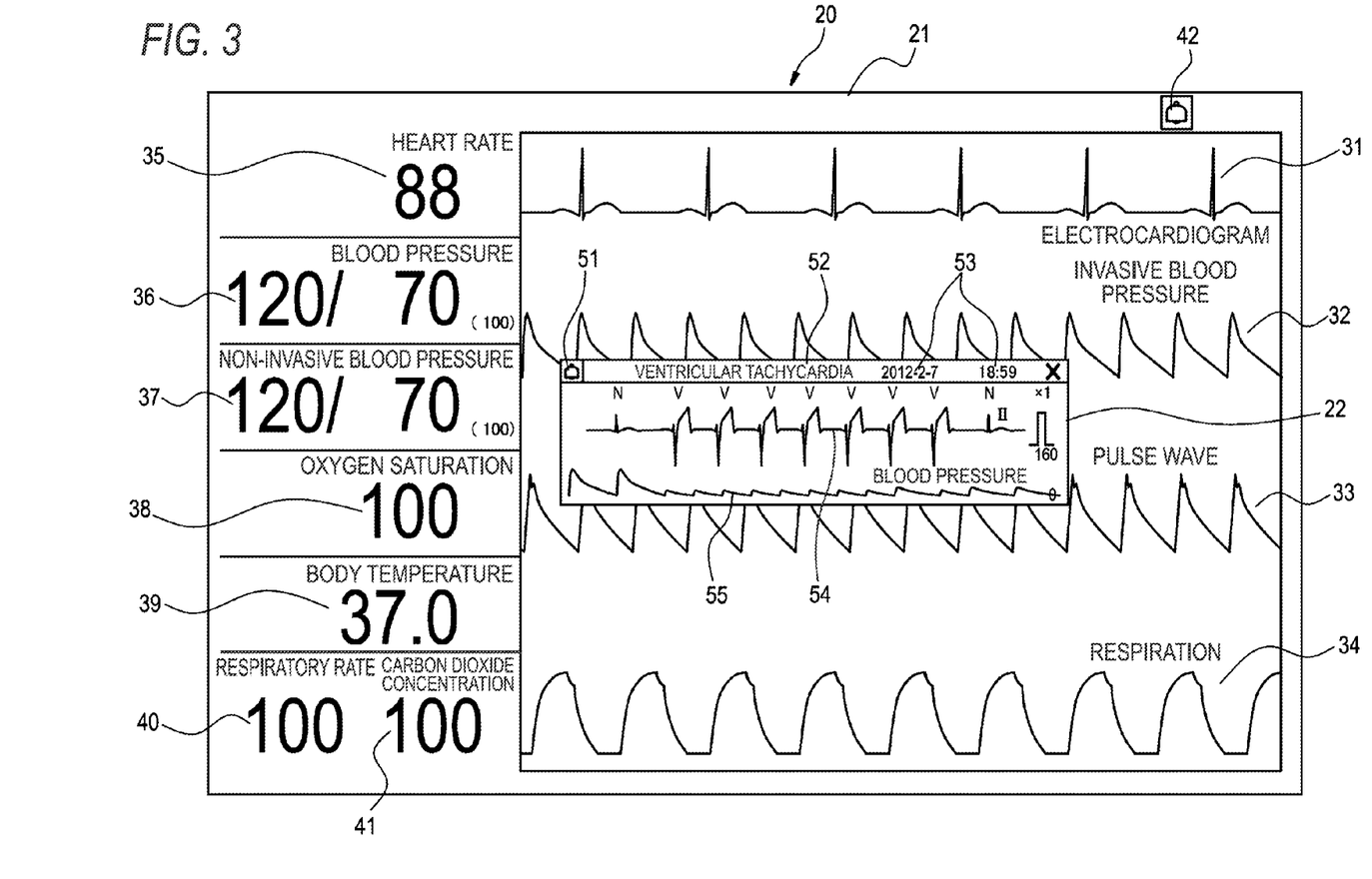
FIG. 3 is a view showing another specific example of biological information of the abnormality display screen which is displayed on the measurement display screen.
Figure 4:
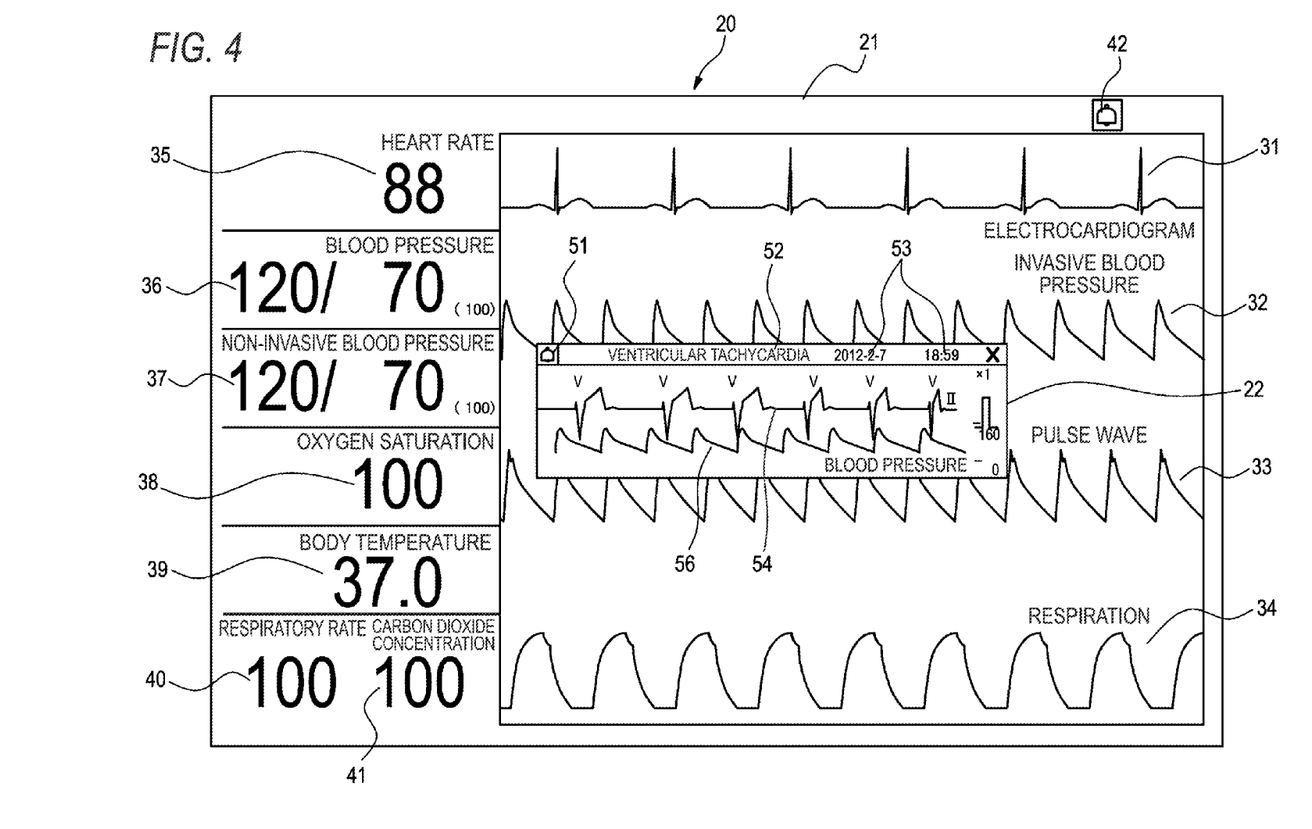
FIG. 4 is a view showing a further specific example of biological information of the abnormality display screen which is displayed on the measurement display screen.

FIGS. 2 to 4 show a state where the abnormality display screen 22 is superimposedly displayed on a part of the display screen area of the measurement display screen 21. Based on the display control signal supplied from the display controlling unit 13, the displaying section 20 displays biological information on the measurement display screen 21 and the abnormality display screen 22.

In one of the specific examples, as shown in FIG. 2, the displaying section 20 displays waveform biological information which is being measured from the subject, and which includes an electrocardiogram waveform 31, an invasive blood pressure waveform 32, a pulse waveform 33, and a respiratory waveform 34, on the measurement display screen 21. Moreover, the displaying section 20 displays numerical biological information including a heart rate 35, an invasive blood pressure value 36, a non-invasive blood pressure value 37, an oxygen saturation 38, a body temperature 39, a respiratory rate 40, and a carbon dioxide concentration 41, on the measurement display screen 21. The alarm symbol 42 indicating that an abnormality occurred in biological information in the past is displayed in an upper right portion of the measurement display screen 21.

Furthermore, the displaying section 20 displays an alarm symbol 51 alarming that an abnormality occurs in biological information, a message 52 indicating the contents of the abnormality, the time and date 53 of the occurrence of the abnormality, and the waveform (here, the electrocardiogram waveform) 54 from which the abnormality is detected, on the abnormality display screen 22. When the message 52 is displayed, it is alarming that an abnormality due to ventricular tachycardia occurs in the electrocardiogram. When the electrocardiogram waveform 54 in which a ventricular tachycardia state is caused is displayed, it is made easy to recognize the number of occurrences of a ventricular premature contraction and the waveform shape, and rapid diagnosis and procedure are enabled. The displaying section 20 causes the abnormality display screen 22 to be displayed at a position where it does not overlap with the electrocardiogram waveform 31 functioning as a target for comparison. The waveform functioning as a target for comparison is a waveform which is identical in kind to the abnormal waveform (here, the electrocardiogram waveform 54) in the plurality of displayed waveforms, i.e., the waveforms 31 to 34 under measurement. The items to be displayed on the abnormality display screen 22, such as waveforms and numerical values may be set by a medical person.

In another one of the specific examples, as shown in FIG. 3, the displaying section 20 displays, similarly with FIG. 2, the waveform biological information including: the electrocardiogram waveform 31; the invasive blood pressure waveform 32; the pulse waveform 33; and the respiratory waveform 34, the numerical biological information including: the heart rate 35; the invasive blood pressure value 36; the non-invasive blood pressure value 37; the oxygen saturation 38; the body temperature 39; the respiratory rate 40; and the carbon dioxide concentration 41, and the alarm symbol 42, on the measurement display screen 21.

Furthermore, the displaying section 20 displays the alarm symbol 51 alarming that an abnormality occurs in biological information, the message 52 indicating the contents of the abnormality, the time and date 53 of the occurrence of the abnormality, the waveform (here, the electrocardiogram waveform) 54 from which the abnormality is detected, and an invasive blood pressure waveform 55 related to the electrocardiogram waveform 54, on the abnormality display screen 22. The displayed invasive blood pressure waveform 55 is acquired at the timing when the abnormality is detected in the electrocardiogram waveform.

When the message 52 is displayed, it is alarming that an abnormality due to ventricular tachycardia occurs in the electrocardiogram. When the electrocardiogram waveform 54 in which a ventricular tachycardia state is caused is displayed, it is made easy to recognize the number of occurrences of a ventricular premature contraction and the waveform shape, and rapid diagnosis and procedure are enabled. When the invasive blood pressure waveform 55 is displayed, it is made easy to determine whether the occurrence of the abnormality in the electrocardiogram waveform is caused by an artifact or not. In the case where ventricular tachycardia occurs, the amount of blood pumped from the ventricle is reduced, and the blood pressure tends to be lowered. An invasive blood pressure waveform is a waveform (biological information) related to an electrocardiogram waveform. When the invasive blood pressure waveform 55 at the timing when the abnormality occurs in the electrocardiogram is observed, therefore, it is possible to determine whether the abnormality of the electrocardiogram waveform 54 is caused by the ventricular tachycardia 52 or not. In the example of FIG. 3, it can be recognized that the blood pressure is lowered, from the invasive blood pressure waveform 55. In the case where the electrocardiogram waveform 54 which is displayed on the abnormality display screen 22 in FIG. 3, consequently, it is possible to determine that a change of an electrocardiogram involving blood pressure reduction occurs, and a diagnosis can be made that the abnormality of the electrocardiogram waveform 54 is caused by the ventricular tachycardia 52.

In a further one of the specific examples, as shown in FIG. 4, the displaying section 20 displays, similarly with FIG. 2, the waveform biological information including: the electrocardiogram waveform 31; the invasive blood pressure waveform 32; the pulse waveform 33; and the respiratory waveform 34, the numerical biological information including: the heart rate 35; the invasive blood pressure value 36; the non-invasive blood pressure value 37; the oxygen saturation 38; the body temperature 39; the respiratory rate 40; and the carbon dioxide concentration 41, and the alarm symbol 42, on the measurement display screen 21.

Furthermore, similarly with FIG. 3, the displaying section 20 displays the alarm symbol 51, the message 52, the time and date 53 of the occurrence of the abnormality, the waveform (here, the electrocardiogram waveform) 54 from which the abnormality is detected, and an invasive blood pressure waveform 56 related to the electrocardiogram waveform 54, on the abnormality display screen 22.

When the message 52 is displayed, it is alarming that an abnormality due to ventricular tachycardia occurs in the electrocardiogram. When the electrocardiogram waveform 54 in which a ventricular tachycardia state is caused is displayed, it is made easy to recognize the number of occurrences of a ventricular premature contraction and the waveform shape. When the invasive blood pressure waveform 56 is displayed, it is made easy to determine whether the occurrence of the abnormality in the electrocardiogram waveform is caused by an artifact or not. In the case where ventricular tachycardia occurs, the amount of blood pumped from the ventricle is reduced, and the blood pressure tends to be lowered. When the invasive blood pressure waveform 56 at the timing when the abnormality occurs is observed, therefore, it is possible to determine whether the abnormality of the electrocardiogram waveform 54 is caused by the ventricular tachycardia 52 or not. In the case of the invasive blood pressure waveform 56 shown in FIG. 4, blood pressure reduction does not occur. In the electrocardiogram waveform shown in FIG. 4, consequently, it is possible to determine that a change of an electrocardiogram not involving blood pressure reduction occurs. The rhythm of the electrocardiogram waveform 54 is different from that of the invasive blood pressure waveform 56. From these phenomena, also a determination that the abnormality of the electrocardiogram waveform 54 is not caused by the ventricular tachycardia 52, and may be caused by an artifact will be necessary.

FIGS. 5A to 7B show other specific examples of biological information displayed on the abnormality display screen 22 of the displaying section 20.

Figure 5A:
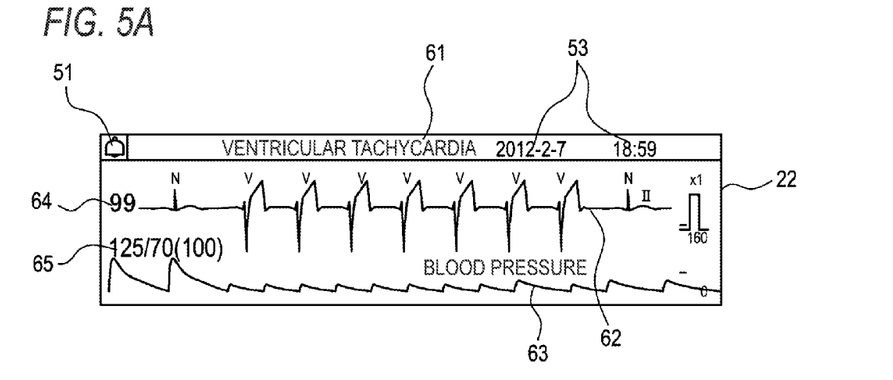
FIGS. 5A, 5B, and 5C are views showing specific combination examples of biological information which is displayed on the abnormality display screen.

FIG. 5A shows a state where the controlling section 10 detects that an abnormality occurs in measurement information of an electrocardiogram, selects blood pressure information (circulation) as biological information related to the electrocardiogram waveform, and causes these sets of biological information to be displayed on the abnormality display screen 22.

Based on the display control signal supplied from the display controlling unit 13, the displaying section 20 displays the alarm symbol 51 alarming that an abnormality occurs in biological information, a message 61 indicating the contents of the abnormality, the time and date 53 of the occurrence of the abnormality, a waveform (here, the electrocardiogram waveform) 62 from which the abnormality is detected, an invasive blood pressure waveform 63 related to the electrocardiogram waveform 62, and a heart rate 64 and blood pressure value 65 at the timing when the abnormality is detected, on the abnormality display screen 22.

When the message 61 is displayed, it is alarming that an abnormality due to ventricular tachycardia occurs in the electrocardiogram. When the electrocardiogram waveform 62 in which a ventricular premature contraction occurs and a ventricular tachycardia state is caused is displayed, it is made easy to recognize the number of occurrences of a ventricular premature contraction and the waveform shape, and rapid diagnosis and procedure are enabled. The invasive blood pressure waveform 63 is displayed as information for determining whether the occurrence of the abnormality in the electrocardiogram waveform is caused by an artifact or not. In the case where ventricular tachycardia occurs, the amount of blood pumped from the ventricle is reduced, and the blood pressure tends to be lowered. When the invasive blood pressure waveform 63 at the timing when the abnormality occurs in the electrocardiogram is observed, therefore, it is possible to determine whether the abnormality of the electrocardiogram waveform 62 is caused by the ventricular tachycardia 61 or not. The blood pressure is lowered in the invasive blood pressure waveform 63. In the electrocardiogram waveform 62, therefore, it is possible to determine that a change of an electrocardiogram involving blood pressure reduction occurs, and a diagnosis can be made that the abnormality of the electrocardiogram waveform 62 is caused by the ventricular tachycardia 61. Moreover, numerical information (the heart rate of 64, and the blood pressure value of 65) is additionally displayed as biological information at the timing when the abnormality is detected, whereby the occurrence of the abnormality can be instantly recognized.

Figure 5B:
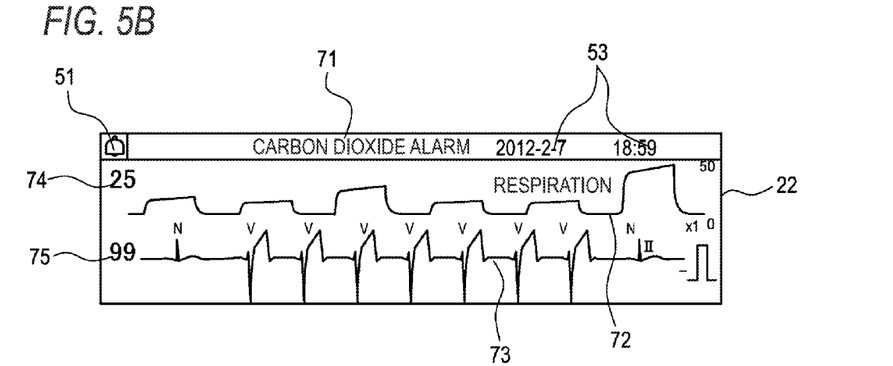

FIG. 5B shows a state where the controlling section 10 detects that an abnormality occurs in measurement information of respiration, selects heart beat information as biological information related to the respiratory waveform, and causes these sets of biological information to be displayed on the abnormality display screen 22.

Based on the display control signal supplied from the display controlling unit 13, the displaying section 20 displays the alarm symbol 51, a message 71 indicating the contents of the abnormality, the time and date 53 of the occurrence of the abnormality, a waveform (here, the respiratory waveform) 72 from which the abnormality is detected, a carbon dioxide concentration 74 at the timing when the abnormality is detected, an electrocardiogram waveform 73 related to the respiratory waveform 72, and the heart rate 75 at the timing when the abnormality is detected, on the abnormality display screen 22.

Figure 5C:
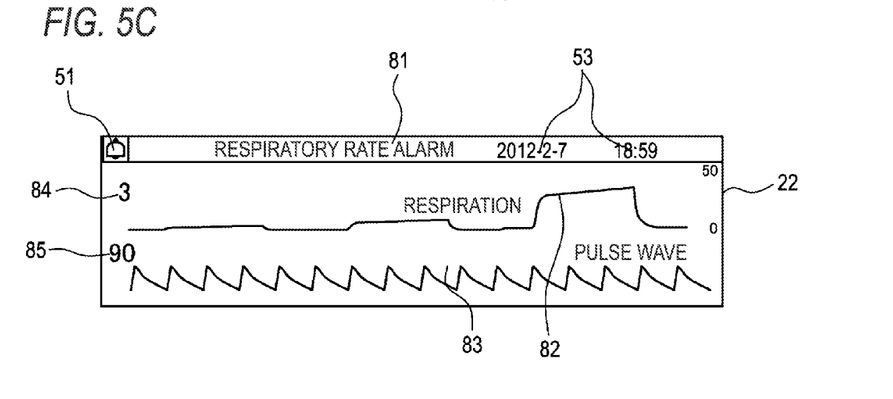

FIG. 5C shows a state where the controlling section 10 detects that an abnormality occurs in measurement information of respiration, selects blood oxygen information as biological information related to the respiratory waveform, and causes these sets of biological information to be displayed on the abnormality display screen 22.

Based on the display control signal supplied from the display controlling unit 13, the displaying section 20 displays the alarm symbol 51, a message 81 indicating the contents of the abnormality, the time and date 53 of the occurrence of the abnormality, a waveform (here, the respiratory waveform) 82 from which the abnormality is detected, a respiratory rate 84 at the timing when the abnormality is detected, a pulse waveform 83 related to the respiratory waveform 82, and an oxygen saturation 85 at the timing when the abnormality is detected, on the abnormality display screen 22. The pulse waveform 83 is a waveform which is acquired by measuring a capacity change that is caused by a flow-in of blood in a blood vessel, and which indicates the vasomotor and indirectly the cardiac activity.

When the message 81 is displayed, it is alarming that an respiratory abnormality occurs. When the respiratory waveform 82 in which the respiration (expiration and inspiration) is disturbed is displayed, it is made easy to recognize the respiratory condition, and it is possible to anticipate the reduction of the oxygen saturation due to apnea. This enables rapid diagnosis and procedure to be performed. When the respiratory rate at the timing when the abnormality is detected is numerically displayed (the respiratory rate of 84), the reduction of the respiratory rate can be instantly recognized. When the pulse waveform 83 and oxygen saturation 85 at the timing when the abnormality is detected are displayed, it is possible to recognize the possibility of symptoms of respiratory failure caused by the reduction of the oxygen saturation which may be caused by the reduction of the respiratory rate. Moreover, the pulse waveform can be used in diagnosis of an influence of apnea such as the increase of the heart rate on the cardiac activity. In this example, the reduction of the respiratory rate involves that of the oxygen saturation, and the reduction of the respiratory function instead of an artifact is actually suspected.

Figure 6A:
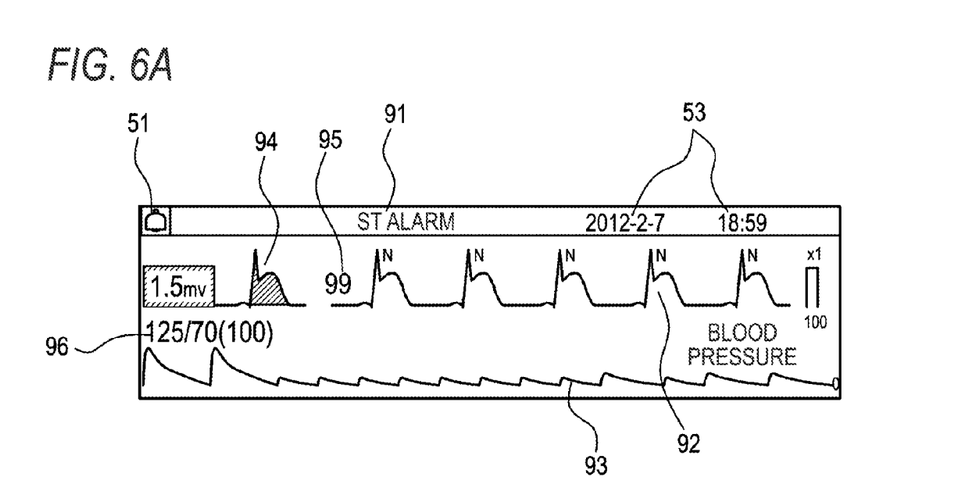
FIGS. 6A, 6B, and 6C are views showing other specific combination examples of biological information which is displayed on the abnormality display screen.

FIG. 6A shows a state where the controlling section 10 detects that an abnormality occurs in the ST segment of the electrocardiogram, selects blood pressure information (circulation) as biological information related to the electrocardiogram waveform, and causes these sets of biological information to be displayed on the abnormality display screen 22.

Based on the display control signal supplied from the display controlling unit 13, the displaying section 20 displays the alarm symbol 51, a message 91 indicating the contents of the abnormality, the time and date 53 of the occurrence of the abnormality, a waveform (here, the electrocardiogram waveform) 92 from which the abnormality is detected, an invasive blood pressure waveform 93 related to the electrocardiogram waveform 92, a waveform 94 that is partially cut out of the electrocardiogram waveform 92 from which the abnormality is detected, and a heart rate 95 and blood pressure value 96 at the timing when the abnormality is detected, on the abnormality display screen 22.

Figure 6B:
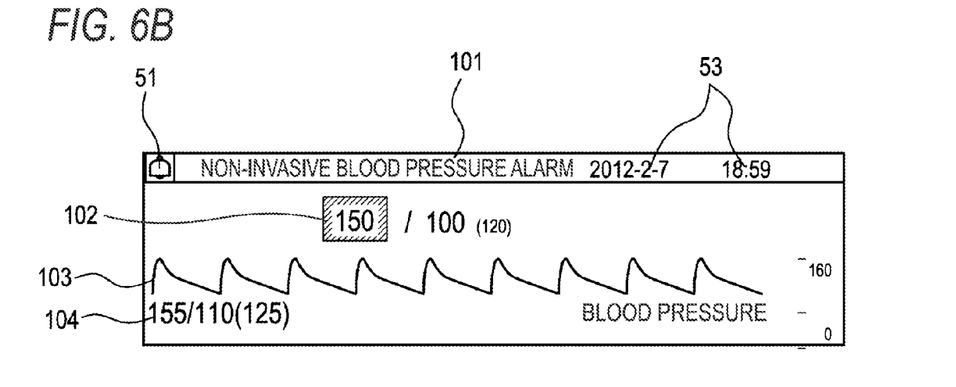

FIG. 6B shows a state where the controlling section 10 detects that an abnormality occurs in the non-invasive blood pressure value, selects blood pressure information as biological information related to the non-invasive blood pressure value, and causes these sets of biological information to be displayed on the abnormality display screen 22.

Based on the display control signal supplied from the display controlling unit 13, the displaying section 20 displays the alarm symbol 51, a message 101 indicating the contents of the abnormality, the time and date 53 of the occurrence of the abnormality, a numerical value (here, the non-invasive blood pressure value) 102 from which the abnormality is detected, an invasive blood pressure waveform 103 related to the non-invasive blood pressure value 102, and an invasive blood pressure value 104, on the abnormality display screen 22.

Figure 6C:
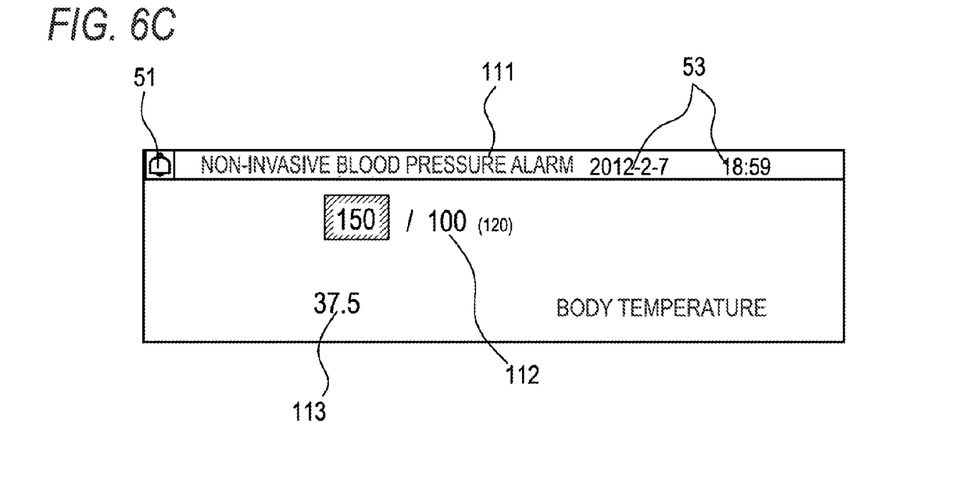

FIG. 6C shows a state where the controlling section 10 detects that an abnormality occurs in the non-invasive blood pressure value, selects body temperature information as biological information related to the non-invasive blood pressure value, and causes these sets of biological information to be displayed on the abnormality display screen 22.

Based on the display control signal supplied from the display controlling unit 13, the displaying section 20 displays the alarm symbol 51, a message 111 indicating the contents of the abnormality, the time and date 53 of the occurrence of the abnormality, a numerical value (here, the non-invasive blood pressure value) 112 from which the abnormality is detected, and a body temperature 113 related to the non-invasive blood pressure value 112, on the abnormality display screen 22.

Figure 7A:
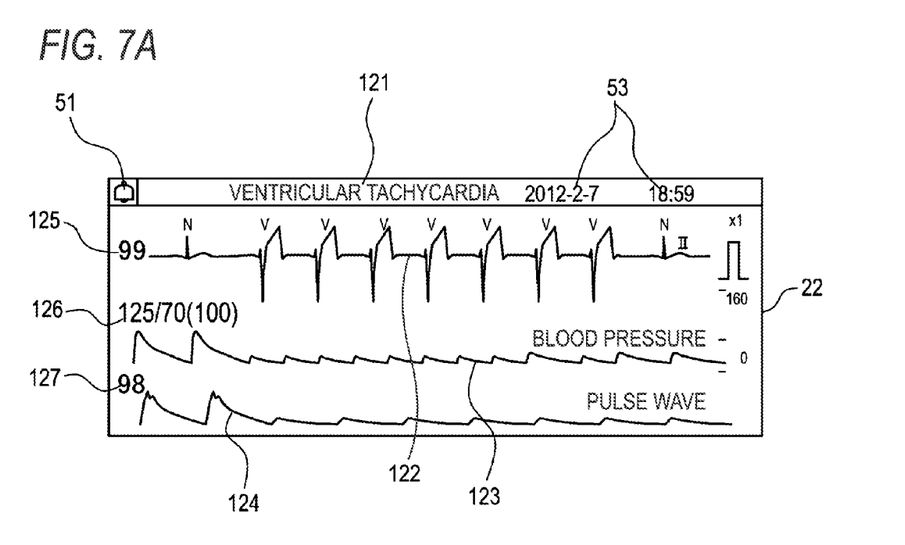
FIGS. 7A and 7B are views showing further specific combination examples of biological information which is displayed on the abnormality display screen.

FIG. 7A shows a state where the controlling section 10 detects that an abnormality occurs in the measurement information of the electrocardiogram, selects blood pressure information (circulation) and blood oxygen information as biological information related to the electrocardiogram waveform, and causes these sets of biological information to be displayed on the abnormality display screen 22.

Based on the display control signal supplied from the display controlling unit 13, the displaying section 20 displays the alarm symbol 51, a message 121 indicating the contents of the abnormality, the time and date 53 of the occurrence of the abnormality, a waveform (here, the electrocardiogram waveform) 122 from which the abnormality is detected, an invasive blood pressure waveform 123 and pulse wave 124 related to the electrocardiogram waveform 122, and a heart rate 125, invasive blood pressure value 126, and oxygen saturation 127 at the timing when the abnormality is detected, on the abnormality display screen 22.

When the message 121 is displayed, it is alarming that an abnormality due to ventricular tachycardia occurs in the electrocardiogram. When the electrocardiogram waveform 122 in which a ventricular premature contraction occurs and a ventricular tachycardia state is caused is displayed, it is made easy to recognize the number of occurrences of a ventricular premature contraction and the waveform shape, and rapid diagnosis and procedure are enabled. The invasive blood pressure waveform 123 is displayed as information for determining whether the occurrence of the abnormality in the electrocardiogram waveform is caused by an artifact or not. In the case where ventricular tachycardia occurs, the amount of blood pumped from the ventricle is reduced, and the blood pressure tends to be lowered. When the invasive blood pressure waveform 123 at the timing when the abnormality occurs in the electrocardiogram waveform is observed, therefore, it is possible to determine whether the abnormality of the electrocardiogram waveform 122 is caused by the ventricular tachycardia 121 or not. The blood pressure is lowered in the invasive blood pressure waveform 123. In the electrocardiogram waveform 122, therefore, it is possible to determine that a change of an electrocardiogram involving blood pressure reduction occurs, and a diagnosis can be made that the abnormality of the electrocardiogram waveform 122 is caused by the ventricular tachycardia 121. The oxygen saturation can be used as an indication in checking the possibility of symptoms of respiratory failure. When the oxygen saturation 127 is displayed, therefore, it is possible to determine the possibility of symptoms of respiratory failure. When the pulse wave 124 is displayed, an influence of the symptoms on the cardiac activity can be rapidly diagnosed, and adequate procedures can be performed. When biological information at the timing when the abnormality is detected is additionally displayed as numerical information (the heart rate of 125, and the invasive blood pressure value of 126), whereby the occurrence of the abnormality can be rapidly recognized. In this example, ventricular tachycardia involves the reduction of the blood pressure and that of the pulse amplitude, and hence it is possible to determine that ventricular arrhythmia which causes a failure of the ventricular function actually occurs.

Figure 7B:
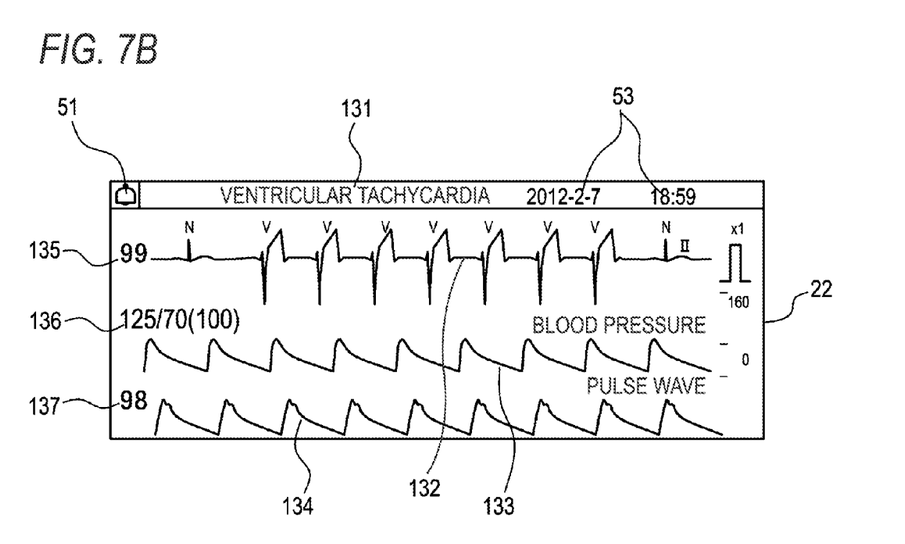

FIG. 7B shows a state where the controlling section 10 detects that an abnormality occurs in the measurement information of the electrocardiogram, selects blood pressure information (circulation) and blood oxygen information as biological information related to the electrocardiogram waveform, and causes these sets of biological information to be displayed on the abnormality display screen 22.

Based on the display control signal supplied from the display controlling unit 13, the displaying section 20 displays the alarm symbol 51, a message 131 indicating the contents of the abnormality, the time and date 53 of the occurrence of the abnormality, a waveform (here, the electrocardiogram waveform) 132 from which the abnormality is detected, an invasive blood pressure waveform 133 and pulse wave 134 related to the electrocardiogram waveform 132, and a heart rate 135, invasive blood pressure value 136, and pulse value 137 at the timing when the abnormality is detected, on the abnormality display screen 22.

When the message 131 is displayed, it is alarming that an abnormality due to ventricular tachycardia occurs in the electrocardiogram. When the electrocardiogram waveform 132 in which a ventricular tachycardia state is caused is displayed, it is made easy to recognize the number of occurrences of a ventricular premature contraction and the waveform shape.

When the invasive blood pressure waveform 133 is displayed, it is possible to determine whether the occurrence of the abnormality in the electrocardiogram waveform is caused by an artifact or not. In the case where ventricular tachycardia occurs, the amount of blood pumped from the ventricle is reduced, and the blood pressure tends to be lowered. When the invasive blood pressure waveform 133 at the timing when the abnormality occurs in the electrocardiogram waveform is observed, therefore, it is possible to determine whether the abnormality of the electrocardiogram waveform 132 is caused by the ventricular tachycardia 131 or not. In the invasive blood pressure waveform 133, the blood pressure is not lowered. In the electrocardiogram waveform 132, therefore, it is possible to determine that a change of an electrocardiogram not involving blood pressure reduction occurs. The pulse waveform 134 is a waveform which shows a capacity change that is caused by a flow-in of blood in a blood vessel, and indicates the vasomotor and indirectly the cardiac activity. It cannot be confirmed that an abnormality exists in the pulse waveform 134. There is no abnormality also in the invasive blood pressure value 136 and the pulse value 137. The rhythm of the electrocardiogram waveform 132 is different from the rhythms of the invasive blood pressure waveform 133 and the pulse wave 134. From these phenomena, it is possible to determine that the abnormality of the electrocardiogram waveform 132 is not caused by the ventricular tachycardia 131, and may be caused by an artifact.

Figure 8A:
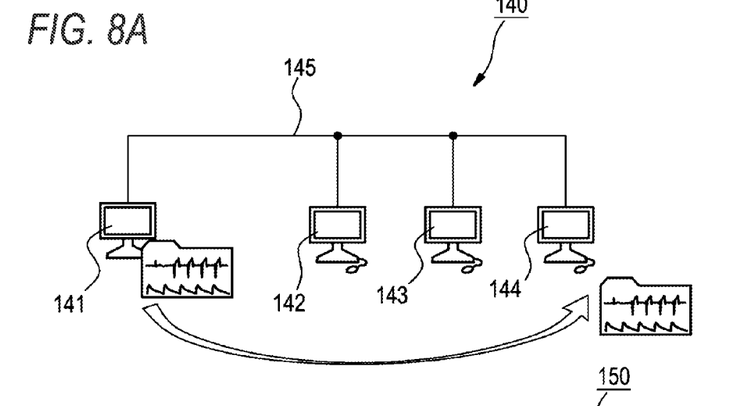
FIGS. 8A, 8B, and 8C are diagrams showing specific examples of a biological information displaying system of the presently disclosed subject matter.
Figure 8B:
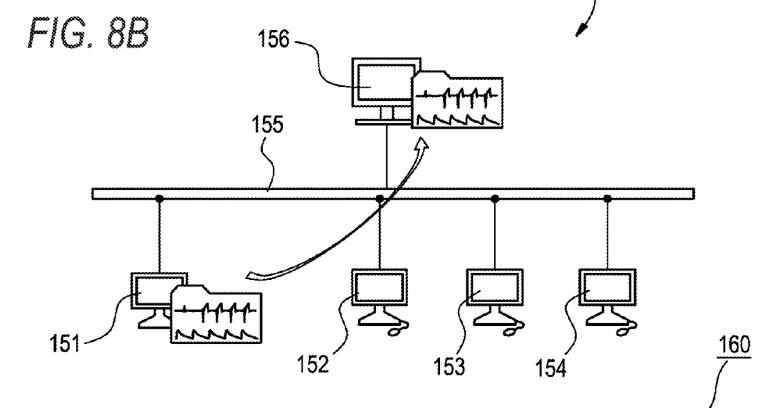
Figure 8C:
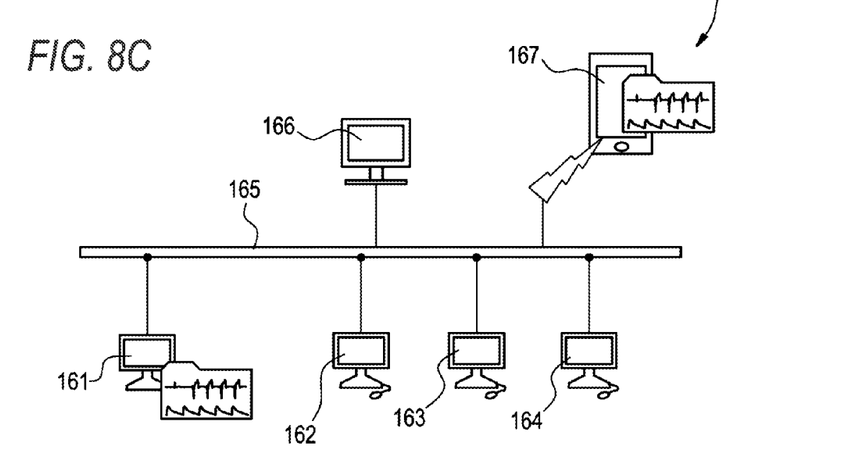

FIGS. 8A to 8C show embodiments of the biological information displaying system. Biological information displaying apparatuses (bedside monitors) shown in the embodiments have similar functions as those of the biological information displaying apparatus 1 which has been described with reference to FIGS. 1 to 7B.

A biological information displaying system 140 shown in FIG. 8A includes a plurality of biological information displaying apparatuses (bedside monitors). The bedside monitors 141 to 144 are disposed at the bedsides of subjects, respectively. The bedside monitors 141 to 144 are connected to one another through a network 145 so that data communication can be performed. On the display screen of each of the bedside monitors, waveforms, numerical values, and the like of biological information of subjects which are measured by the other bedside monitors can be displayed. A medical person or the like can designate biological information which is measured by any one of the bedside monitors, to be displayed on the display screen. In order that, when an abnormality occurs in biological information of a certain subject, a medical person who is in the vicinity of a bedside monitor in a separate place can recognize the occurrence, an alarm (sound, a lamp, a message, or the like) indicating that an abnormality occurs may be displayed on the display screens of the bedside monitors in synchronization with the occurrence of the abnormality.

In a biological information displaying system 150 shown in FIG. 8B, in addition to a plurality of bedside monitors 151 to 154, a central monitor 156 is connected to a network 155. The central monitor 156 is disposed in a nurses' station, a waiting room for doctors, or the like, and enables biological information of subjects to be centrally monitored. Biological information measured by the bedside monitors 151 to 154 is transmitted to the central monitor 156 through the network 155. The transmitted biological information is held in a storage section of the central monitor 156. In the case where an abnormality occurs in the biological information measured by the bedside monitors 151 to 154, similarly with the biological information displaying apparatus 1 which has been described with reference to FIGS. 1 to 7B, information indicating that the abnormality is alarmed, biological information at the timing when the abnormality occurs, and the like are displayed also on the display screen of the central monitor 156. In addition, also the kind of the display screen to be displayed on the central monitor 156, the display mode, and the like are similar to those of the biological information displaying apparatus 1. For example, the display contents are not erased even when the abnormality resolves, and are continuously displayed until a confirming process is executed in response to an external operation.

In a biological information displaying system 160 shown in FIG. 8C, in addition to a plurality of bedside monitors 161 to 164, a central monitor 166 and a portable communication terminal 167 such as a smartphone are connected to a network 165. Similarly with the central monitor 166, biological information measured by the bedside monitors 161 to 164 is transmitted also to the portable communication terminal 167 through the network 165. In the case where an abnormality occurs in the biological information measured by the bedside monitors 161 to 164, similarly with the biological information displaying apparatus 1 which has been described with reference to FIGS. 1 to 7B, information indicating that the abnormality is alarmed, biological information at the timing when the abnormality occurs, and the like are displayed also on the display screen of the portable communication terminal 167. In addition, also the kind of the display screen to be displayed on the portable communication terminal 167, the display mode, and the like are similar to those of the biological information displaying apparatus 1. For example, the display contents are not erased even when the abnormality resolves, and are continuously displayed until a confirming process is executed in response to an external operation.

The biological information displaying apparatus and biological information displaying system of the presently disclosed subject matter are configured as described above, and therefore have the following functions and effects.

The abnormality display screen is superimposedly displayed on the measurement display screen, the display contents include information indicating that an abnormality is alarmed, biological information at the timing when the abnormality occurs, and the like, and, even the abnormality resolves, the displayed abnormality display screen is not erased, and continued to be displayed until a confirmation process is executed in response to an external operation. Therefore, it is possible to surely prevent an alarm which indicates an occurrence of an abnormality, and which was issued in the past, from being missed, and the importance of the contents of the alarm can be promptly determined.

The biological information to be measured includes a plurality of kinds of measurement items (waveforms and numerical value data of the heart rate, the electrocardiogram waveform, the blood pressure value, the blood oxygen saturation, the inspiration oxide concentration, the body temperature, and the like). When an abnormality of biological information is detected, the numerical value and waveform of the abnormality are displayed on the abnormality display screen, and also the numerical value and waveform of other biological information which may cause the abnormality of the biological information, or those of other biological information which may be changed in accordance with the abnormality of the biological information, i.e., those of biological information related to the biological information in which the abnormality occurs are displayed on the abnormality display screen. Based on a plurality of sets of necessary biological information, therefore, a medical person can comprehensively diagnose the condition of the subject, and apply adequate treatment to the subject. When dynamics of a plurality of parameters are observed, it is made easy to determine whether an occurrence of an abnormality is caused by an artifact or not, and it is possible to perform a diagnosis instantly and correctly.

The abnormality display screen is displayed in synchronization with the abnormality detection by the controlling section, and the displayed contents are continued to be displayed until a confirmation process is executed. Unless a confirmation process is executed, therefore, a medical person can easily confirm the display contents of the abnormality display screen without performing any operation on the screen, and it is possible to surely prevent an occurrence of an abnormality from being missed.

Bedside monitors, central monitor, and portable communication terminal such as a smartphone which constitute the biological information displaying system are connected to one another through a network. Even when a medical person is in a place remote from a concerned subject, therefore, the person can check biological information of the subject, and perform sure determination and rapid treatment.

The presently disclosed subject matter is not limited to the above-exemplified embodiments, and may be embodied while variously modified without departing the spirit of the presently disclosed subject matter.

According to an aspect of the presently disclosed subject matter, an alarm which was issued in the past can be surely prevented from being missed, the contents of the alarm are correctly known, and a procedure can be rapidly performed.

What is claimed is:

1. A biological information displaying apparatus comprising:
    a displaying section on which a measurement display screen and an abnormality display screen are displayed, the measurement display screen displaying biological information under measurement, the abnormality display screen displaying information providing notice of an abnormality of the biological information, and the biological information including a waveform at a timing when the abnormality occurs; and
    a display controlling section which is configured to control the displaying section, the display controlling section which is configured to display the abnormality display screen on the measurement display screen, based on a preset alarm condition, so that at least a part of the abnormality display screen is superimposed on the measurement display screen, wherein,
    in a case where the abnormality display screen is displayed on the displaying section, the display controlling section controls the displaying section so that, even when the abnormality resolves, the information providing notice of the abnormality of the biological information, and the biological information including the waveform at the timing when the abnormality occurs are continued to be displayed on the abnormality display screen, and
    the display controlling section controls the displaying section so that the abnormality display screen is continued to be displayed until a confirmation process for the abnormality display screen is executed in response to an external operation, and
    the confirmation process includes an alarm confirmation process indicating that an alarm is confirmed, and a content confirmation process indicating that contents of the information providing notice of the abnormality of the biological information and the biological information including the waveform at the timing when the abnormality occurs which are displayed on the abnormality display screen are confirmed.

2. The biological information displaying apparatus according to claim 1, wherein,
    in the case where the abnormality display screen is displayed on the displaying section, the display controlling section controls the displaying section so that the information alarming providing notice of the abnormality of the biological information, and the biological information at the timing when the abnormality occurs are continued to be displayed on the abnormality display screen, until the confirmation process is executed in response to the external operation.

3. The biological information displaying apparatus according to claim 1, wherein
    the biological information includes first biological information and second biological information which are different from each other,
    the abnormality occurs in the first biological information,
    the first biological information is related to the second biological information, and
    the display controlling section controls the displaying section so that the second biological information is displayed on the abnormality display screen in addition to the first biological information.

4. The biological information displaying apparatus according to claim 3, wherein
    the first biological information and the second biological information are displayed on the abnormality display screen by a waveform and a numerical value.

5. The biological information displaying apparatus according to claim 3, wherein
    the first biological information which is displayed on the abnormality display screen is an electrocardiogram waveform, and
    the second biological information includes at least an invasive blood pressure waveform.

6. The biological information displaying apparatus according to claim 1, wherein
    the abnormality display screen is superimposed on a part of the measurement display screen.

7. A biological information displaying system incorporating a plurality of biological information displaying apparatuses according to claim 1, wherein
    the plurality of biological information displaying apparatuses are connected to a network, and biological information displayed in each of the biological information displaying apparatuses is displayable in another biological information displaying apparatus connected to the network.

* * * * *